(12) United States Patent
Kothandaraman et al.

(10) Patent No.: US 8,729,323 B2
(45) Date of Patent: May 20, 2014

(54) PRODUCTION OF HYDROCARBON FROM HIGH FREE FATTY ACID CONTAINING FEEDSTOCKS

(75) Inventors: Geetha Kothandaraman, Bartlesville, OK (US); Sundararajan Uppili, Bartlesville, OK (US); Jianhua Yao, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 838 days.

(21) Appl. No.: 12/959,084

(22) Filed: Dec. 2, 2010

(65) Prior Publication Data
US 2011/0152588 A1 Jun. 23, 2011

Related U.S. Application Data

(60) Provisional application No. 61/289,558, filed on Dec. 23, 2009.

(51) Int. Cl.
*C07C 1/00* (2006.01)

(52) U.S. Cl.
USPC .............................. 585/240; 585/242; 44/605

(58) Field of Classification Search
CPC .......... C10G 3/42; C10G 17/00; C10G 45/58; C10G 2300/1011; C10G 2300/1055; C10G 2300/20; C10G 2300/205
USPC .................................... 585/240, 242; 44/605
See application file for complete search history.

(56) References Cited

U.S. PATENT DOCUMENTS

| | | |
|---|---|---|
| 3,313,859 A | 4/1967 | Doane |
| 3,816,483 A | 6/1974 | Werdehausen et al. |
| 4,224,144 A | 9/1980 | Hensley et al. |
| 2004/0168830 A1 | 9/2004 | Reddy et al. |
| 2008/0289247 A1* | 11/2008 | Irving .............................. 44/307 |

FOREIGN PATENT DOCUMENTS

WO 2005095565 A1 10/2005

OTHER PUBLICATIONS

"Fatty acid Amides, IV. Reactiono f Rates with Ammonia and Amines", Roe et al., The Journal of the American Oil Chemists Society Jan. 1952.*
Bachur et al., "Microsomal Synthesis of Fatty Acid Amides", Journal of Biological Chemistry, 1966, vol. 241, No. 6, pp. 1308-1313; p. 1308, col. 2, para 3.
PCT/US10/59514 International Search Report and Written Opinion (Form PCT/ISA/220) dated Feb. 7, 2011.

* cited by examiner

*Primary Examiner* — Nina Bhat
(74) *Attorney, Agent, or Firm* — Phillips 66 Company

(57) ABSTRACT

There is provided a process for converting high free fatty acid containing feedstock such as acidulated soapstock into hydrocarbon compound especially fuel range hydrocarbons using amidation as a pretreatment step followed by hydroprocessing.

21 Claims, No Drawings

PRODUCTION OF HYDROCARBON FROM HIGH FREE FATTY ACID CONTAINING FEEDSTOCKS

CROSS-REFERENCE TO RELATED APPLICATIONS

This application is a non-provisional application which claims benefit under 35 USC §119(e) to U.S. Provisional Application Ser. No. 61/289558 filed Dec. 23, 2009, entitled "PRODUCTION OF HYDROCARBON FROM HIGH FREE FATTY ACID CONTAINING FEEDSTOCKS" which is incorporated herein in their entirety.

STATEMENT OF FEDERALLY SPONSORED RESEARCH

None

FIELD OF THE DISCLOSURE

The present invention relates generally to a process for converting free fatty acid into hydrocarbon compound, especially fuel range hydrocarbons.

BACKGROUND OF THE DISCLOSURE

There is a national interest in the discovery of alternative sources of fuels and chemicals, other than from petroleum resources. As the public discussion concerning the availability of petroleum resources and the need for alternative sources continues, government mandates will require fuel range hydrocarbons to include, at least in part, hydrocarbons derived from sources besides petroleum. As such, there is a need to develop alternative sources for hydrocarbons useful for producing fuels and chemicals.

One possible alternative source of hydrocarbons for producing fuels and chemicals is the natural carbon found in plants and animals, such as for example, oils and fats. These so-called "natural" carbon resources (or renewable hydrocarbons) are widely available, and remain a target alternative source for the production of hydrocarbons. For example, it is known that oils and fats has been successfully hydrotreated to produce hydrocarbons/fuel range hydrocarbons which is also called "Renewable fuel" such as renewable diesel fuels.

Compared to vegetable oil or animal fat, there are many cheap low-cost and waste by-products of the food industry that are readily available in the market. For example, acidulated soapstock is a by-product of soybean oil degumming with a very high fatty acid content (>88%) and could be a potential feedstock for renewable diesel production. However, the product suffers from high metals and acid content which makes it difficult for direct hydroprocessing.

High acid content has been addressed by converting the fatty acids into esters with the use of alkaline catalysts and methanol as a solvent. However, esterification reactions are equilibrium processes that require vast excess of solvent. Though fatty acid methyl esters are directly being used as bio-diesel in the market, they suffer from stability and quality issues.

As such, development of a new pretreatment methodology that would solve the issue of high acid content present in low-cost renewable feedstock and renders such feedstock suitable for hydroprocessing to renewable hydrocarbon could be a significant contribution to the art and to the economy.

BRIEF DESCRIPTION OF THE DISCLOSURE

The present invention relates generally to a process for converting high free fatty acid containing feedstock such as acidulated soapstock into hydrocarbon compound especially fuel range hydrocarbons using amidation as a pretreatment step followed by hydroprocessing.

The pretreatment involves the reaction of acidulated soapstock with ammonia/amine to produce a solid fatty amide product that can be physically separated from the reaction medium. The production of the solid amide also separates the high metals associated with the feedstock providing a neutral, low metal feedstock suitable for traditional hydroprocessing in the refinery.

In one embodiment, there is provided a process for converting a free fatty acid containing feedstock to hydrocarbon, the process comprising: a) providing a feedstock comprising at least one free fatty acid; b) reacting the feedstock with ammonia/amine to produce a first product mixture comprising solid fatty amide; c) subjecting the product mixture to a separation device whereby the solid fatty amide is separated from the first product mixture; and d) reacting the solid fatty amide with a hydroprocessing catalyst in a reaction zone under a condition sufficient to produce a second product mixture comprising hydrocarbon and ammonia.

This invention solves the issue of high acid content present in low-cost renewable feedstocks making it suitable for traditional hydroprocessing in the refinery. This invention also provides value to a waste by-product of the food industry avoiding the food vs. fuel debate for biofuels.

Other objects, advantages and embodiments of the invention will be apparent from the following detailed description of the invention and the appended claims.

DETAILED DESCRIPTION OF EMBODIMENTS OF THE INVENTION

According to one embodiment of the current invention, there is provided a process for converting a free fatty acid containing feedstock to hydrocarbon, the process comprising: a) providing a feedstock comprising at least one free fatty acid; b) reacting the feedstock with ammonia/amine to produce a first product mixture comprising solid fatty amide; c) subjecting the product mixture to a separation device whereby the solid fatty amide is separated from the first product mixture; and d) reacting the solid fatty amide with a hydroprocessing catalyst in a reaction zone under a condition sufficient to produce a second product mixture comprising hydrocarbon and ammonia.

The free fatty acids containing feedstock may be contacted with ammonia/primary amine in accordance with the present invention to produce a product mixture comprising solid fatty amide.

The term, "free fatty acid," is used generally to refer to any carboxylic acid having the general formula RCOOH, where R is an alkyl group that may vary in chain length. Any suitable free fatty acid containing feedstock can be used in this application. Example of free fatty acids containing feedstock useful in the present invention includes, but are not limited to yellow grease (used restaurant oil), brown grease, animal fats, vegetable oils, algae oils, palm fatty acid distillates, jatropha oil and the like and mixtures and combinations thereof The amount of free fatty acid present in the feedstock may vary. Generally, the free fatty acids are present in an amount in the range of from about 0.1 to about 100 percent by weight, based on the total weight percent of the mixture. In one embodiment of the present invention, the free fatty acids is present in an amount of from about 2 weight percent to about 80 weight percent, based on the total weight of the mixture. In another embodiment of the present invention, the free fatty acids are present in an amount of from 5 to 75 weight percent.

The acid content of the hydrocarbon product is measured by the total acid number or "TAN." The total acid number (TAN), as used herein, is defined as milligrams of potassium hydroxide (KOH) necessary to neutralize the acid in 1 gram of oil and is determined using ASTM test method D 644-95 (Test Method for Neutralization Number by Potentiometric Titration). Generally, the total acid number for a yellow grease feed stock is in the range of greater than about 2 mgKOH/g. In accordance with the present invention, the total acid number for the hydrocarbon product produced in accordance with the present invention will be less than the TAN of the yellow grease included in the original feedstock.

The term, ammonia/amine is used generally to refer to any organic compound containing a basic nitrogen atom with a lone pair of electrons having the general formula of R-NR1-R2. where R1 and R2=H, alkyl or hydroxyl alkyl groups with varying chain lengths. Any suitable amine can be used in this application. Example of mono and multi-functional amine useful in the present invention includes, but are not limited to Monoethanolamine, diethanolamine, methylamine, ethylamine and the like and mixtures and combinations thereof.

The ratio of the amount of primary amine to the amount of the free fatty acid containing feedstock is in the range of from about 10:1 to about 1:1. based on the total mole ratio. In one embodiment of the present invention, such ratio is 5:1. In another embodiment of the present invention, such ratio is 1:1.

The solid fatty amide produced here is generally referring to any amide compounds having the general formula RCO-NR1R2. Various types solid fatty amide can be produced in this application. Example of solid fatty amide according to the present invention includes, but are not limited to oleamide, myristamide, stearamide, arachidamide, palmitamide, lauramide, capramide, caprylamide, and the like and mixtures and combinations thereof.

Generally, the reaction between ammonia/primary amine and free fatty acid containing feedstock results in the production of solid fatty amide which when hydroprocessed releases ammonia . . . According to one embodiment, the ammonia may be recycled back to the reaction for further amide production.

Generally, the free fatty acids may be reacted with ammonia/primary amine under the conditions at which the temperature is maintained in the range of from about 20° C. to 300° C. In another embodiment, the temperature is maintained in the range of from about 50° C. to 250° C. In addition, the free fatty acids may be reacted with ammonia/primary amine under the conditions at which the pressure is maintained in the range of from about 0 psig to 200 psig. In another embodiment, the pressure is maintained in the range of from about 0 psig to 250 psig.

Generally, solid fatty amide may then be contacted with a catalyst composition under a condition sufficient to produce a reaction product containing diesel boiling range hydrocarbons. Examples of suitable catalysts include hydrotreating catalysts. The term "hydrotreating" as used herein, generally describes a catalyst that is capable of utilizing hydrogen to accomplish saturation of unsaturated materials, such as aromatic and olefinic compounds.

Useful catalyst compositions for the hydrotreating process include any catalysts which may effective in the conversion of solid fatty amide to hydrocarbons (e.g. renewable diesel) when contacted under suitable reaction conditions. Examples of suitable catalysts include hydrotreating catalysts. Examples of hydrotreating catalysts useful in one embodiment of the present invention include, but are not limited to, materials containing compounds selected from Group VI and Group VIII metals, and their oxides and sulfides. Examples of suitable support materials for the hydrogenation catalysts include, but are not limited to, silica, silica-alumina, aluminum oxide ($Al_2O_3$), silica-magnesia, silica-titania and acidic zeolites of natural or synthetic origin. Examples of hydrotreating catalysts include but are not limited to alumina supported cobalt-molybdenum, nickel sulfide, nickel-tungsten, cobalt-tungsten and nickel-molybdenum.

According to one embodiment of the present invention, the reaction zone may comprise any suitable type of reactor. Exemplary reactors include fixed bed reactors and fluidized bed reactors. Generally, the reaction conditions at which the reaction zone is maintained generally include a temperature in the range of from about 260° C. to about 430° C. In another embodiment, the temperature is in the range of from about 300° C. to about 400° C. The reaction conditions at which the reaction zone is maintained generally include a pressure between about 100 psig to about 2000 psig, and more particularly between about 100 psig to about 750 psig. In one embodiment employing a fixed bed reactor, the pressure is maintained between about 100 psig to about 350 psig. In one embodiment employing a fluidized bed reactor, the pressure is maintained between about 400 psig to about 750 psig.

Typical diesel fuel components comprise liquid hydrocarbon middle distillate fuel oils, for instance petroleum jet or turbine fuels, automotive diesel fuels, railroad diesel fuels, heating oils and gas oil They will typically have boiling points within the usual diesel range of 150° C. to 400° C., depending on grade and use.

The following examples are presented to further illustrate the present invention and are not to be construed as unduly limiting the scope of this invention.

EXAMPLE 1

In the lab-scale testing, stoichiometric amounts of acidulated vegetable oil (calculated based on free fatty acid content) and monoethanolamine (1:08-12M ratio) were mixed in round-bottomed flask and heated from 165-240° C., at atmosphere pressure in air for 2-6 hours, followed by vacuum removal of excess water (at 30-65 mm Hg) for 3-12 hours. The resulting liquid was cooled into a waxy solid with a melting point of 60-70° C. The material was confirmed to be a primary amide based on H1-NMR and FT-IR.

This material was dissolved in xylenes and hydrogenated under standard hydrodesulfurization (HDS) conditions. An example run was carried out using a standard commercial NiMo type hydrotreating catalyst at 340° C., 600 psig with a LHSV (liquid hourly space velocity) of 1.0. The product was characterized by gas chromatography analysis, and was shown to be C12-C18 linear paraffins (diesel range).

It is therefore discovered that this invention solves the issue of high TAN present in low-cost renewable feedstocks making it suitable for traditional hydroprocessing in the refinery. This invention also provides value to a waste by-product of the food industry avoiding the food vs. fuel debate for biofuels.

One of the major advantages to this process is the production of a solid amide which can be physically separated from the reaction mixture, yet dissolvable in hydrocarbon for the further conversion into fuel range hydrocarbons. The other advantage of this process is that the ammonia/amine used for the synthesis of amide is released back as ammonia during hydroprocessing and can be recycled. Additional ammonia or other chemicals will not be required for the pretreatment process once it is initiated.

The results shown in the above examples, clearly demonstrate that the present invention is well adapted to carry out the objects and attain the ends and advantages mentioned as well as those inherent therein. Reasonable variations, modifications and adaptations may be made within the scope of this disclosure and the appended claims without departing from the scope of the invention. While this invention has been described in detail for the purpose of illustration, it should not be construed as limited thereby but intended to cover all changes and modifications within the spirit and scope thereof.

That which is claimed:

1. A process for converting a free fatty acid containing feedstock to hydrocarbon, the process comprising:
   a. providing a feedstock comprising at least one free fatty acid;
   b. reacting said feedstock with ammonia/amine to produce a first product mixture comprising solid fatty amide;
   c. subjecting said product mixture to a separation device whereby said solid fatty amide is separated from said first product mixture; and
   d. reacting said solid fatty amide with a hydroprocessing catalyst in a reaction zone under a condition sufficient to produce a second product mixture comprising hydrocarbon and ammonia.

2. The process of claim 1 further comprising a step of recycling said ammonia and amide from said second product mixture back to said step b.

3. The process of claim 1 further comprising a step of dissolving said solid fatty amide separated from said first product mixture prior to step d.

4. The process of claim 1, wherein said free fatty acid is any carboxylic acid having molecular formula of RCOOH, wherein R is an alkyl group that may vary in chain length.

5. The process of claim 1, wherein said free fatty acid is selected from the group consisting of vegetable oils, yellow grease, animal fats, brown grease, algae oil, palm fatty acid distillates, vegetable oils, jatropha oil, and any mixtures thereof.

6. The process of claim 1, wherein said free fatty acid is present in said feedstock in an amount in the range of from about 0.01 to about 100 weight percent based on the total weight of said feedstock.

7. The process of claim 1, wherein said free fatty acid is present in said feedstock in an amount in the range of from about 2 to about 80 weight percent based on the total weight of said feedstock.

8. The process of claim 1, wherein said ammonia/amine having the molecular formula of R-NR1R2, where in R1 and R2=H, alkyl or hydroxyl alkyl groups with varying chain lengths.

9. The process of claim 1, wherein said amine is selected from the group consisting of monoethanolamine, diethanolamine, methylamine, ethylamine, and any mixture and combinations thereof.

10. The process of claim 1, wherein the ratio of the amount of said amine to the amount of said free fatty acid containing feedstock is in the range of from about 10:1 to about 1:1 based on the total mole ratio.

11. The process of claim 1, wherein the ratio of the amount of said amine to the amount of said free fatty acid containing feedstock is about 5:1 based on the total mole ratio.

12. The process of claim 1, wherein said solid fatty amide having the molecular formula of (R-CO-NR1R2).

13. The process of claim 1, wherein said solid fatty amide is selected from the group consisting of oleamide, myristamide, stearamide, arachidamide, palmitamide, lauramide, capramide, caprylamide, and any mixtures and combinations thereof.

14. The process of claim 1, wherein said step b is carried out at a temperature in the range of from about 20° C. to about 300° C.

15. The process of claim 1, wherein said step b is carried out at a pressure in the range of from about 0 to about 250 psig.

16. The process of claim 1, wherein said step d is carried out at a pressure in the range of from 100 to 2000 psig and a temperature in the range of from about 260° C. to about 430° C.

17. The process of claim 1, wherein said step d is carried out at a pressure in the range of from 100 to 750 psig and a temperature in the range of from about 300° C. to about 400° C.

18. The process of claim 1, wherein said hydrotreating catalyst comprises cobalt and molybdenum or nickel and molybdenum.

19. The process according to claim 1, wherein said catalyst comprises cobalt and molybdenum or nickel and molybdenum on a zeolite support.

20. The process of claim 1, wherein said separation device is selected from the group consisting of a centrifuge, settling tanks, filtration, any other physical solid liquid separation device, and any combination thereof.

21. The process of claim 1, wherein said hydrocarbon is selected from the group consisting of gasoline, naphtha, jet fuel, kerosene, diesel fuel, light cycle oil, vacuum gas oil, atmospheric gas oil, atmospheric tower bottom, and combinations of any two or more thereof.

* * * * *